US008877981B2

(12) United States Patent
Zacchi et al.

(10) Patent No.: US 8,877,981 B2
(45) Date of Patent: Nov. 4, 2014

(54) INTEGRATED PROCESS FOR PREPARING ACROLEIN AND 3-METHYLMERCAPTOPROPIONALDEHYDE

(71) Applicants: Pablo Zacchi, Huerth (DE); Caspar Finkeldei, Alzenau (DE); Martin Koerfer, Kahl (DE)

(72) Inventors: Pablo Zacchi, Huerth (DE); Caspar Finkeldei, Alzenau (DE); Martin Koerfer, Kahl (DE)

(73) Assignee: Evonik Industries AG, Essen (DE)

( * ) Notice: Subject to any disclaimer, the term of this patent is extended or adjusted under 35 U.S.C. 154(b) by 0 days.

(21) Appl. No.: 13/927,430

(22) Filed: Jun. 26, 2013

(65) Prior Publication Data

US 2014/0005437 A1 Jan. 2, 2014

Related U.S. Application Data

(60) Provisional application No. 61/668,750, filed on Jul. 6, 2012.

(30) Foreign Application Priority Data

Jun. 27, 2012 (EP) ..................................... 12173892

(51) Int. Cl.
 C07C 323/22 (2006.01)
 C07C 45/28 (2006.01)
 C07C 319/18 (2006.01)
 C07C 319/02 (2006.01)

(52) U.S. Cl.
 CPC ............... *C07C 319/02* (2013.01); *C07C 45/28* (2013.01); *C07C 319/18* (2013.01)
 USPC ............................................. 568/63; 568/41

(58) Field of Classification Search
 USPC .................................................... 568/41, 63
 See application file for complete search history.

(56) References Cited

U.S. PATENT DOCUMENTS

| | | | |
|---|---|---|---|
| 2,626,282 | A | 1/1953 | Cunningham et al. |
| 4,225,516 | A | 9/1980 | Biola et al. |
| 4,319,047 | A | 3/1982 | Komorn et al. |
| 5,352,837 | A | 10/1994 | Hsu et al. |
| 5,744,647 | A | 4/1998 | Hsu et al. |
| 5,905,171 | A | 5/1999 | Hsu |
| 6,031,138 | A | 2/2000 | Hsu et al. |
| 6,057,481 | A | 5/2000 | Brockwell et al. |
| 6,187,963 | B1 | 2/2001 | Etzkorn et al. |
| 6,320,076 | B1 | 11/2001 | Hsu et al. |
| 7,531,066 | B2 | 5/2009 | Gros et al. |
| 2002/0173677 | A1 | 11/2002 | Hsu et al. |
| 2005/0103616 | A1 | 5/2005 | Gros |
| 2012/0165573 | A1* | 6/2012 | Finkeldei et al. ............... 568/41 |
| 2013/0231501 | A1 | 9/2013 | Hasselbach et al. |
| 2013/0245318 | A1 | 9/2013 | Steffan et al. |

FOREIGN PATENT DOCUMENTS

| | | |
|---|---|---|
| DE | 2627430 | 12/1976 |
| DE | 102010064250 | 6/2012 |
| EP | 0 022 697 A1 | 1/1981 |
| WO | WO9429254 | 12/1994 |
| WO | WO 97/00858 | 1/1997 |
| WO | WO 97/36848 A1 | 10/1997 |
| WO | WO 03/068721 A1 | 8/2003 |

OTHER PUBLICATIONS

U.S. Appl. No. 14/067,098, filed Oct. 30, 2013, Finkeldei, et al.
Search Report issued Dec. 3, 2012 in European Application No. 12173892.6 (With English Translation of Category of Cited Documents).
International Search Report and Written Opinion of the International Searching Authority issued Oct. 1, 2013, in PCT/EP2013/062206 (with English Translation of Categories of Cited Documents).

\* cited by examiner

*Primary Examiner* — Sudhakar Katakam
*Assistant Examiner* — Pancham Bakshi
(74) *Attorney, Agent, or Firm* — Oblon, Spivak, McClelland, Maier & Neustadt, L.L.P.

(57) ABSTRACT

A process to produce 3-methylmercaptopropionaldehyde is provided. The process comprises: A) oxidizing a mixture of propylene and inert diluent gases with air over a heterogeneous catalyst to obtain a gaseous oxidation reaction mixture comprising acrolein and by-products; B) quenching the gaseous oxidation reaction mixture to obtain a gas stream comprising acrolein and a quench liquid comprising residual acrolein and the by-products; C) stripping the acrolein from the by-products of the quench liquid and returning the stripped acrolein to the quench; D) absorbing a first portion of the gas stream comprising acrolein from the quench B) in water to obtain an aqueous acrolein solution and an uncondensable gaseous stream comprising inert gases; D1) recycling at least a portion of the uncondensable gaseous stream to the oxidation A) to supply the inert diluent gases; E) distilling the acrolein from the aqueous acrolein solution to obtain an acrolein-free aqueous bottom product; E1) condensing the distilled acrolein; F) reacting the distilled acrolein E1) and the gas stream comprising acrolein B) with methyl mercaptan in a mixture comprising at least one of 3-methylmercaptopropionaldehyde and a hemithioacetal of methyl mercaptan and 3-methylmercaptopropionaldehyde to obtain the 3-methylmercaptopropionaldehyde.

32 Claims, 2 Drawing Sheets

INTEGRATED PROCESS FOR PREPARING ACROLEIN AND 3-METHYLMERCAPTOPROPIONALDEHYDE

CROSS REFERENCE TO RELATED APPLICATIONS

This application claims priority to European Patent Application No. 12173892.6, filed Jun. 27, 2012, and to U.S. Provisional Application No. 61/668,750, filed Jul. 6, 2012, the disclosures of which are incorporated herein by reference in their entireties.

BACKGROUND OF THE INVENTION

4-Thiapentanal (3-(methylthio)propionaldehyde, 3-methylmercaptopropionaldehyde) (MMP), is a substance which is used principally as a starting material for the chemical synthesis of the amino acid D,L-methionine or what is called methionine hydroxy analogue (2-hydroxy-4-(methylthio)butyric acid). The standard route for the preparation of MMP is the reaction between methyl mercaptan (MC) and acrolein (AC).

The basic acrolein process, which is based on the partial oxidation of propylene, is conventionally known (see Arntz, D., Fischer, A., Höpp, M., Jacobi, S., Sauer, J., Ohara, T., Sato, T., Shimizu, N., Schwind, H., Acrolein and Methacrolein, Ullmann's Encyclopedia of Industrial Chemistry, Wiley-VCH Verlag, 2007, particularly pages 7-9) and consists principally of a reaction step, a quench/by-product removal step and an absorption/distillation step. In order to further purify the product (for example the removal of volatile compounds, such as acetaldehyde), one or more extra distillation steps can be employed. The partial oxidation reaction is generally conducted in a salt-cooled fixed bed reactor at operating temperatures of 300 to 400° C. The reactor is equipped with tubes filled with a particulate catalyst, and is kept at the required temperatures by circulating liquid salt which is cooled at a later stage in a heat exchanger, generally by raising of steam. The propylene and air feed streams are normally diluted with inert diluent gases such as nitrogen, steam, carbon dioxide or mixtures thereof. Hydrocarbons which do not exhibit any significant reaction on the catalyst under the normal reaction conditions, such as the saturated hydrocarbon propane, may likewise be part of the mixture. The dilution of the mixture is performed in order to moderate the peak temperatures in the catalyst bed and in order to minimize the risk of formation of explosive mixtures. The reactor is normally equipped with a post-cooling stage (the cooling medium is generally a liquid salt) in which the temperature of the gaseous mixture is lowered to 200-280° C., before it enters the quench stage of the first column. In this subsequent process step, the mixture is contacted with water in order to achieve a rapid temperature reduction. At this point, the majority of the condensation of the water produced during the oxidation reaction and of the water which is (possibly) added as a diluent to the reaction feed mixture also takes place. Downstream of the quench zone of the column, the acrolein-rich gas flows upwards in the column and comes into contact with a falling water stream, which has the task of removing unwanted by-products, mainly acrylic acid and acetic acid and other impurities. The falling water film originates from the condensation of water in the upper part of the column, which is operated at temperatures of 8 to 25° C., preferably of 10 to 20° C. Additional water streams can optionally be supplied to the upper part of the column in order to achieve a more favourable liquid-to-gas ratio. The by-products removed leave the column together with the condensed water via the bottom and are detoxified by thermal or biological means after they have passed through the stripping column, in order to reduce the acrolein content of this stream as far as possible. The acrolein is removed from the gas stream which leaves the upper part of the first column in a downstream processing stage, by absorption in a suitable medium (normally an aqueous solution). The liquid obtained at the base of the apparatus, generally an absorption column, is fed into a distillation column in which the low-boiling acrolein is separated from the high-boiling absorption medium and is recovered in liquid form. If water is used as the absorption medium, a product close to the azeotropic concentration is obtained as the top product. The main impurity present is acetaldehyde, while other reaction by-products are found in very small or trace amounts. The acrolein can be conveyed in this form to storage tanks, or can be subjected to further workup in order to increase the purity thereof by lowering the content of accompanying by-products. In view of the low oxygen content thereof, the uncondensable low-acrolein gas which leaves the absorption step through the upper part of the column can be recycled at least partly into the reactor as a source of inert material. The remaining low-acrolein gas is normally passed to an incineration unit for the disposal or detoxification thereof. The partial oxidation reaction is generally not conducted up to full conversion of the propylene feed in order to achieve the maximum possible acrolein yields. The propylene not converted in the reaction stage passes through the quench/by-product removal step and leaves the absorber via the top together with the other uncondensable gases. The use of a fraction of these low-acrolein gases as a dilution medium for the reaction mixture also achieves the additional positive effect of returning a fraction of the unconverted propylene to the reaction stage. In this way, the overall conversion of this raw material under the most suitable reaction conditions increases, which leads to a higher overall acrolein yield.

Acrolein is a very toxic, inflammable, very reactive substance having a great tendency to highly exothermic polymerization reactions. For this latter reason, a stabilizer to counteract free-radical polymerization is added in several stages in the process and prior to storage.

In order principally to reduce the safety risks in connection with the storage of acrolein, several alternative production/purification concepts have been proposed. Since the main use of acrolein is the production of MMP, the concepts generally include the reaction of acrolein to give MMP without any significant intermediate storage. For example, U.S. Pat. No. 7,531,066 describes a process similar to the above-described standard process, except that, instead of obtaining acrolein in liquid form as the top product of the distillation step, a partial condensation is conducted and the remaining gaseous acrolein is reacted directly in a further stage with liquid or gaseous methyl mercaptan in the presence of a catalyst to give MMP.

U.S. Pat. No. 5,352,837 (or WO94/29254) and U.S. Pat. No. 5,744,647 describe a process for the production of MMP, in which acrolein is first produced by the partial oxidation of propylene or propane in a reaction unit, then the reaction gases are cooled in order to remove water and by-products, and the remaining gas stream comprising principally uncondensable constituents and acrolein is contacted with liquid MMP in the downstream processing step in order to retain acrolein in the liquid phase and, in this same medium, to react the acrolein with methyl mercaptan in the presence of a catalyst to form MMP. Compared to the conventional acrolein process, the process described in U.S. Pat. No. 5,352,837 and U.S. Pat. No. 5,744,647 offers the advantage that liquid acrolein need not be isolated and stored intermediately. However, the process is characterized in that it has no partial recycling of the low-oxygen gases which leave the acrolein absorption step. The inert material required to dilute the reaction mixture before it enters the reactor is water vapor (steam) in this case. These large amounts of steam which are fed into the reactor are condensed in the quench step and leave the process together with the acid by-products (principally acrylic acid and acetic acid). Compared to the above-described conventional acrolein process, this process entails the disadvantage that it has significantly higher waste water treatment/disposal costs. Furthermore, the overall acrolein yields, based on the hydrocarbon supplied to the process, are generally lower compared to the standard process. As already mentioned, the reaction, for achievement of good acrolein yields, is not normally conducted up to full conversion of the propylene supplied. Higher propylene conversion rates than the ideal range for the catalyst used give rise to higher proportions of by-products. As already mentioned, in the conventional acrolein production process, a proportion of the unconverted propylene is recycled into the reactor step as a constituent of the low-oxygen gases for the purpose of diluting the feed gas mixture. The recycling of a fraction of the hydrocarbon supplied back to the reactor with the recycle gas stream enables operation close to the ideal single-pass conversion in order to maximize the acrolein yield, while, at the same time, the overall hydrocarbon conversion of this expensive starting material is increased compared to a single-pass unit. In other words, a shortcoming of this recycling stream is that the process described in U.S. Pat. No. 5,352,837 (or WO94/29254) and U.S. Pat. No. 5,744,647 has a lower starting material efficiency (less acrolein—or MMP—per hydrocarbon unit supplied) than the conventional acrolein production process. The use of steam as an inert gas source in the last processes described may arise from the disinclination to recycle the low-oxygen gas which leaves the absorption stage back to the reactor, since this gas contains certain amounts of sulphur compounds which would adversely affect the heterogeneous acrolein catalyst, can accumulate in the system or can form unwanted by-products, which would entail considerable disadvantages.

U.S. Pat. No. 4,225,516 or DE2627430 describes a process for the preparation of MMP, in which, according to the examples, a reaction gas containing 48.2 mol % of water, 41.6 mol % of $N_2$, 5.55 mol % of acrolein and 0.65 mol % of acrylic acid is fed into an acrylic acid removal unit, is cooled later to about 0° C., in order to remove water, and then runs through an absorption unit in which the acrolein is absorbed in MMP. The MMP enters the upper part of the column at temperatures of about −10° C. The mixture of MMP and acrolein obtained in the bottom of the column is passed through a reactor in which the acrolein reacts with methyl mercaptan in the presence of a catalyst. In this process, methyl mercaptan is added continuously to the reactor. The gases which leave the absorption unit are fed into the incineration unit. The presence of large amounts of water in the reaction gas mixture which enters the purification stage of the process indicates that the source of inert material for the acrolein reaction is steam. Just like in the process described in U.S. Pat. No. 5,352,837 and U.S. Pat. No. 5,744,647, the large amount of water which is fed into the reactor, compared to the standard acrolein production process, leads to larger amounts of waste water and hence to higher treatment/disposal costs. Moreover, since no unconverted propylene is recycled to the reactor, the entire acrolein yield based on the hydrocarbon supplied is generally lower than in the standard process. This leads to a higher specific consumption of the hydrocarbon (propylene/propane) supplied per mole of acrolein (or MMP) obtained, which is a great disadvantage of these processes.

DE-102010064250.9 describes a process for the production of MMP, in which acrolein which is obtained by the partial oxidation of propylene in the gas phase first passes through a quench/by-product removal step, then is absorbed in MMP and reacts with free methyl mercaptan or with methyl mercaptan released from the 3-methylmercaptopropionaldehyde/methyl mercaptan hemithioacetal (MMP/MC hemithioacetal, from MC+MMP) formed as an intermediate to give MMP. This invention makes use of methyl mercaptan containing a relatively high level of impurities (dimethyl sulphide, dimethyl ether), and of a homogeneous or heterogeneous catalyst for the MMP reaction. In this process, the inert material fed into the reactor consists of a mixture of nitrogen, carbon dioxide and small amounts of steam. Compared to the processes using steam as the main source of inert gas, as described above, this process has the advantage that much smaller amounts of liquid wastewater are produced, but the disadvantage of a greater offgas stream, which likewise includes organic sulphur compounds. The amount of the offgas stream is also much higher compared to the standard acrolein process. Furthermore, since there is no recycling of propylene to the reaction step, this invention has a lower propylene utilization and hence a smaller amount of acrolein (or MMP) produced per molar unit of hydrocarbon supplied compared to the standard acrolein process.

It was therefore an object of the present invention to provide an integrated process for preparing acrolein by catalytic gas phase oxidation of propylene with oxygenous gas and further reaction of the acrolein produced with methyl mercaptan to give MMP, which has the disadvantages of the known processes only to a reduced degree, if at all.

More particularly, the process according to the invention should work in a very energy-efficient manner with maximum acrolein and MMP yields, i.e. should have minimum energy and steam consumption and minimum waste streams, but at the same time ensure preparation of acrolein in maximum yield based on the amounts of propylene used and, as a result, of MMP of maximum purity and in maximum yield.

SUMMARY OF THE INVENTION

These and other objects are achieved by the present invention, the first embodiment of which includes a process to produce 3-methylmercaptopropionaldehyde, comprising:

A) oxidizing a mixture of propylene and inert diluent gases with air over a heterogeneous catalyst to obtain a gaseous oxidation reaction mixture comprising acrolein and by-products;

B) quenching the gaseous oxidation reaction mixture to obtain a gas stream comprising acrolein and a quench liquid comprising residual acrolein and the by-products;

C) recovering the acrolein by stripping from the quench liquid in a lower portion of the quench B) and returning the stripped acrolein to the quench B);

D) absorbing a first portion of the gas stream comprising acrolein from the quench B) in water to obtain an aqueous acrolein solution and an uncondensable gaseous stream comprising inert gases;

D1) recycling at least a portion of the uncondensable gaseous stream to the oxidation A) to supply the inert diluent gases;

E) distilling the acrolein from the aqueous acrolein solution to obtain an acrolein-free aqueous bottom product;

E1) condensing the distilled acrolein from E);

F) reacting the distilled acrolein from E1) and a second portion of the gas stream comprising acrolein from B) with methyl mercaptan in a mixture comprising at least one of 3-methylmercaptopropionaldehyde and a hemithioacetal of methyl mercaptan and 3-methylmercaptopropionaldehyde to obtain the 3-methylmercaptopropionaldehyde.

In a second embodiment, the present invention includes process to produce 3-methylmercaptopropionaldehyde, comprising:

A and A1) oxidizing a mixture of propylene and inert diluent gases with air over a heterogeneous catalyst in two streams to obtain a first A) and a second A1 gaseous oxidation reaction mixtures comprising acrolein and by-products;

B) quenching the first gaseous oxidation reaction mixture from A) to obtain a gas stream comprising acrolein and a quench liquid comprising residual acrolein and the by-products;

B1) quenching the second gaseous oxidation reaction mixture from A1) to obtain a gas stream comprising acrolein and a quench liquid comprising residual acrolein and the by-products;

C) recovering the acrolein by stripping from the quench liquid in a lower part of the quench B) and returning the stripped acrolein to the quench;

D) absorbing a first portion of the gas stream comprising acrolein from the quench B) in water to obtain an aqueous acrolein solution and an uncondensable gaseous stream comprising inert gases;

D1) recycling at least a portion of the uncondensable gaseous stream to the oxidation streams of A) and A1) to supply the inert diluent gases;

E) distilling the acrolein from the aqueous acrolein solution from D) to obtain an acrolein-free aqueous bottom product;

E1) condensing the distilled acrolein from E);

F) reacting the distilled acrolein from E1) and the gas stream comprising acrolein B1) with methyl mercaptan in a mixture comprising at least one of 3-methylmercaptopropionaldehyde and a hemithioacetal of methyl mercaptan and 3-methylmercaptopropionaldehyde to obtain the 3-methylmercaptopropionaldehyde.

DETAILED DESCRIPTION OF THE INVENTION

Figure 1:
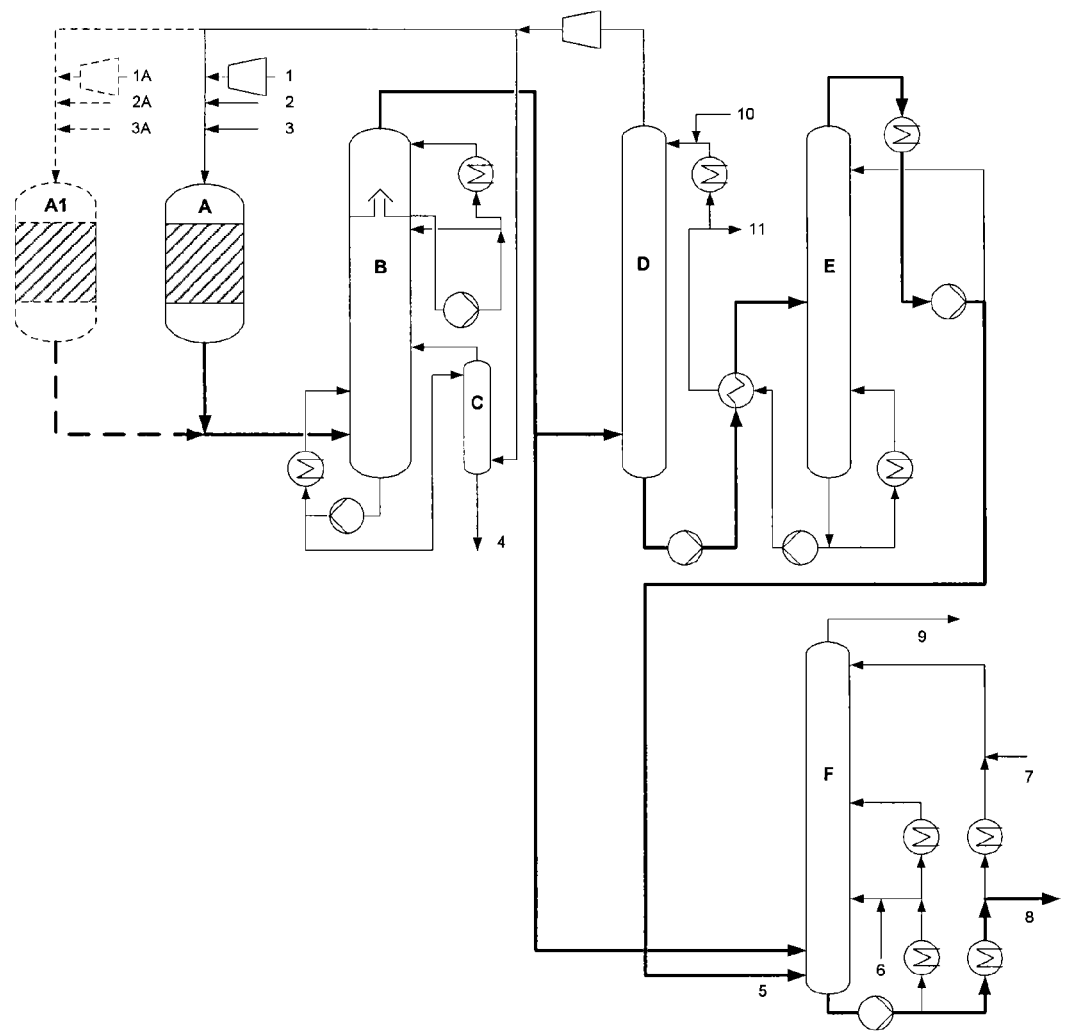
FIG. 1 shows the process flow diagram of the first embodiment according to the invention.

The present invention provides a process for preparing MMP from acrolein and methyl mercaptan, in which the following steps are performed successively:

A) gas phase oxidation of propylene with the aid of air over a heterogeneous catalyst in the presence of a diluent gas;

B) collecting the acrolein-containing gas stream from A) in a quench stage for removal of by-products, for example acrylic acid, acetic acid, formaldehyde or conversion products thereof;

C) recovering the residual acrolein fractions from the liquid present in the lower part of the quench stage B) by stripping, especially from a liquid stream drawn therefrom, and after dividing the acrolein-containing gas stream into at least two streams;

D) collecting a first portion of the acrolein-containing gas stream from the quench stage B) in an absorption stage in the presence of water to obtain an aqueous acrolein solution;

D1) at least partly recycling the uncondensable gas from D) as dilution or inertization gas into reaction stage A);

E) distillatively removing the acrolein from the aqueous acrolein solution from D) in a distillation stage;

E1) condensing the acrolein-containing distillate from E) and supplying the distillate to a reaction stage F) and feeding a further portion of the acrolein-containing gas stream from the quench stage B) directly into the reaction stage F) and F) reaction with methyl mercaptan in the presence of MMP and/or MMP/MC hemithioacetal.

The process according to the present invention has the particular advantage over the conventional standard processes (configuration A-Table 1) that it enables, with about the same acrolein yields and about the same amount of offgases, a somewhat smaller amount of waste water with a simultaneous distinct decrease in the consumption of demineralized water and a distinct reduction in steam consumption and in cooling energy in the form of cooling tower water or cooled water (Table 1). In addition, the storage of liquid acrolein may be avoided, which offers a considerable advantage with regard to lower capital costs and avoidance of hazardous substance storage.

Compared to DE102010064250.9, this invention additionally has the advantage of higher acrolein yields with low cooling tower water consumption and much smaller amounts of offgas and correspondingly much lower offgas treatment costs. More particularly, it is advantageous that the process according to the invention enables production and utilization of an internal dilution or inertization gas stream from absorption stage D, and thus minimization of the consumption of additional inertization gas such as nitrogen, steam or other inert gases, for example methane, natural gas or propane. Inert gases in this context are gases which do not react over the catalyst under the customary production conditions.

According to a second embodiment, the present invention, a process for preparing MMP from acrolein and methyl mercaptan, in which the following steps are performed successively:

A) gas phase oxidation of propylene with the aid of air over a heterogeneous catalyst in the presence of a diluent gas in a first reaction unit and A1) simultaneous gas phase oxidation of propylene with the aid of air over a heterogeneous catalyst in the presence of a diluent gas in a further reaction unit B) collecting the acrolein-containing gas stream from A) in a quench stage with cooling for removal of by-products, for example acrylic acid, acetic acid, formaldehyde or conversion products thereof, B1) collecting the acrolein-containing gas stream from A1) in a parallel quench stage for corresponding removal of by-products, C) recovering the residual acrolein fractions from the liquid present in the lower part of the quench stage B) by stripping, especially from a liquid stream withdrawn therefrom, D) collecting at least a portion of the acrolein-containing gas stream from the quench stage B) in an absorption stage in the presence of water to obtain an aqueous acrolein solution, D1) at least partly recycling the uncondensable gas from D), which also contains as yet unconverted propylene into reaction stages A) and A1) as a diluent or inertization gas, E) distillatively removing the acrolein from the aqueous acrolein solution from D) in a distillation stage, E1) condensing the acrolein-containing distillate from E) and supplying the distillate to a reaction stage F), and feeding the acrolein-containing gas stream from the quench stage B1) directly into the reaction stage F) for F) reaction with methyl mercaptan in the presence of MMP and/or MMP/MC hemithioacetal.

The process according to the second embodiment has the particular advantage over the conventional standard processes (configuration A-Table 1), analogously to the first embodiment, that it enables, with about the same acrolein yields and about the same amount of offgases, a somewhat smaller amount of wastewater with a simultaneous distinct decrease in the consumption of demineralized water and a distinct reduction in steam consumption and in cooling energy in the form of cooled water (Table 1). Equally, the storage of liquid acrolein is avoided, which offers a considerable advantage with regard to lower capital costs and avoidance of hazardous substance storage. Furthermore, it offers the advantage of integrating the benefits of the process of DE102010064250.9, more particularly the rapid and efficient direct reaction of the gaseous acrolein with MC to MMP, and at the same time a saving in power consumption compared to DE102010064250.9 (process configuration D-Table 1).

Compared to DE102010064250.9, inventive process according to the second embodiment, analogously to process option 1, also has the advantage of higher acrolein yields and much smaller amounts of offgas and correspondingly lower offgas treatment costs. It is likewise advantageous that the process according to the invention enables production and utilization of an internal dilution or inertization gas stream from absorption stage D), and thus minimization of the consumption of additional inertization gas such as nitrogen, steam or other inert gases, for example methane, natural gas or propane.

A process is preferably characterized in that step A) and step A1) are each performed in a shell-and-tube reactor whose tubes comprise the catalyst. In the shell-and-tube reactor, the partial oxidation reaction then proceeds to give acrolein. Instead of a single shell-and-tube reactor, it may also be possible to operate several reactors in parallel, and thus a maximum space-time yield may be obtained.

Preference may be given to using a salt bath for cooling of the shell-and-tube reactor, since the temperature can be controlled here very reliably. The salt bath may preferably be kept at a temperature of 300 to 400° C. in order to ensure the best possible conversion and selectivity. The pressure which is established ranges typically from 1.3 to 3 bara. The gases supplied, air, propylene diluent gas and steam, therefore have to be brought to the pressure level required by a compression stage beforehand.

In addition, the process may preferably be conducted such that each of the acrolein-containing gas streams from A) and from A1) passes into the corresponding step B) and B1) respectively at a temperature of 200-280° C. The required cooling of the gas may advantageously be accomplished with the aid of a post-cooling stage.

Preferably, a substream of the condensate present in the upper third of each quench column B and B1 is removed there and, optionally after cooling, preferably to <20° C., fed back to the top of the respective column B or B1 (upper pumped circulation). On the way to the upper part of the column, the reaction gas is contacted with a water stream flowing in countercurrent, and this further reduces the amount of by-products in the gas stream. The water stream originates from the condensation which takes place during the further cooling of the reaction gas to <20° C. in the upper section of the column (upper pumped circulation).

Additionally preferably, a substream of the liquid condensed in the bottom of each quench column B and B1 is removed there and, after cooling, fed back to the lower third of the respective column B or B1 (lower pumped circulation). A large fraction of the by-products, principally acrylic acid and acetic acid, is retained in the condensed liquid and leaves the quench column through the bottom. As a result of the simultaneous circulation of the liquid by means of a pumped circulation system and external cooling, the liquid is simultaneously utilized as a cooling medium for quenching of the reaction gas (lower pumped circulation). The liquid stream which leaves the quench column is preferably pumped to the upper part of a stripper column (C) in which a large fraction of the dissolved residual acrolein is recovered. The residual liquid may then, for example, be fed into a thermal oxidation stage or a biological treatment unit for disposal.

To increase the yield, the recovered residual acrolein fractions from step C) are preferably recycled into step B).

The absorption stage D is operated preferably at temperatures of 1 to 25° C., more preferably of 3 to 15° C., in order to ensure maximum absorption of the acrolein.

The distillation stage E is preferably operated at a pressure of 0.4 to 1.2 bara (bar absolute) and at the temperatures which are established, for example of typically 25 to 65° C., at the top of the column. This ensures that an acrolein-rich mixture with water close to the azeotropic composition is obtained via the upper part of the column, and a virtually acrolein-free water stream via the bottom of the column.

It is additionally preferred that the acrolein-free aqueous bottom product of the distillation is recycled to the absorption stage D, in order to require a minimum amount of additional water therein, while simultaneously reducing the wastewater burdens.

For reaction step F, the addition of methyl mercaptan onto acrolein, preference may be given to using a base-containing catalyst, more preferably an amine, most preferably in a mixture with an acid. This ensures a high conversion rate and a high selectivity of MMP formation. As a result of its generally good solubility, the catalyst acts as a homogeneous catalyst. A small excess of approx. 1.005 mol of methyl mercaptan/mol of acrolein may be preferred, to ensure a high conversion of the acrolein.

3) The base used is preferably an optionally substituted N-heterocyclic amine or an amine of the formula NR1R2R3 where R1, R2 and R3 are the same or different and are each independently H, C1-C14-alkyl or C7-C14-aralkyl, with the proviso that, when R1, R2 or R3 is H, the two other radicals in each case must not be H. Thus, only one of R1, R2 and R3 may be H.

Particularly suitable bases include, for example, pyridine, alkyl-substituted pyridine, preferably picoline or lutidine, trimethylamine, triethylamine, tripropylamine, tributylamine, tridecylamine, tridodecylamine or dimethylbenzylamine.

Particularly suitable acids include mineral acids, preferably hydrochloric acid, sulphuric acid or phosphoric acid, or organic acids, preferably formic acid, acetic acid, propionic acid, lactic acid, succinic acid, tartaric acid or citric acid.

The reaction in reaction stage F is preferably conducted at a pressure of 1.0 to 2.5 bara and at temperatures of 50 to 100° C., preferably at 60 to 90° C., more preferably at 75-85° C.

It may be additionally preferred that the further portion of the acrolein-containing gas stream from quench stage B), which is conducted directly into reaction stage F), corresponds to an amount of 30-70% by weight, preferably of 40-60% by weight and more preferably of 45-55% by weight, especially of approx. 50% by weight, of the total amount of the acrolein-containing gas from B). This enables particularly low consumptions of cooling energy and of steam compared to the standard production process (configuration A in Table 1). The inventive reaction regime, especially the simultaneous use of liquid and gaseous acrolein fractions, achieves a higher MMP yield than in the process according to DE 10 2010 064 250.9, which is a further advantage in an industrial scale process.

Particular preference may also be given to a process according to the first embodiment, wherein the gas phase oxidation of propylene in step A is executed in parallel in at least one further reactor (A1).

Particular preference is further also given to a process wherein the collection of the acrolein-containing gas stream from A1 for removal of by-products is accomplished in a further quench stage B1.

In summary, important advantages of the process according to the invention (configuration B, C, Table 1) may include the following:
compared to the acrolein/MMP standard process (configuration A, Tab. 1):
no storage of acrolein
approx. 50% less steam consumption
approx. 50% less consumption of demineralized water
lower consumption of cooling energy
similar amount of offgas, but now containing traces of sulphur compounds (good disposability);
compared to MMP/steam inertization (configuration E, Table 1):
amount of wastewater more than 50% smaller
steam consumption almost 40% smaller
higher acrolein yield
smaller amount of offgas (containing sulphur compounds);
compared to DE 10 2010 064 250.9 ("MMP-Kombi" configuration D, Table 1)
amount of offgas approx. 50% smaller (containing sulphur compounds, good disposability)
higher steam consumption in the process
higher acrolein yield
lower power consumption
no external source of dilution/inertization gas required
Description of Process According to FIG. 1

In a preferred form of the invention (cf. FIG. 1 corresponding to a process option 1), the gaseous hydrocarbon (3), preferably propylene, is supplied together with compressed ambient air (1), small amounts of steam (2) and a low-oxygen recycling gas to a shell-and-tube reactor in which the partial oxidation reaction proceeds to give acrolein. Instead of one shell-and-tube reactor, it is also possible to operate several reactors in parallel, in each case preferably with separate propylene, air and steam feed lines (referred to here as 3A, 1A and 2A respectively). As well as acrolein, by-products such as acrylic acid, acetic acid, formaldehyde, acetaldehyde, carbon dioxide, carbon monoxide, and small amounts of other compounds, may be formed in the oxidation reaction. The temperature of the cooling salt may be held at 300 to 400° C. Downstream of the reaction zone, the gas mixture may preferably be cooled in an integrated post-cooler, which may be water-cooled or preferably salt-cooled, and enters the first column (quench column B). As in the above-described conventional acrolein process, in this plant section, the gas mixture is contacted with large amounts of water in order to further cool the hot gases. The majority of the steam present in the mixture, which results principally as a by-product of the oxidation reactions, is condensed in this stage of the process. A large fraction of the by-products, principally acrylic acid and acetic acid, is retained in the condensed liquid and leaves the quench column B through the bottom. This liquid is likewise circulated by a pumped circulation system and is thus utilized as a cooling medium for quenching of the reaction gas (lower pumped circulation). On the way to the upper part of the column, the reaction gas is contacted with an aqueous stream flowing in countercurrent, which further reduces the amount of by-products in the gas stream. The water stream originates from the condensation which takes place during the further cooling of the reaction gas to <20° C. in the upper section of the column (upper pumped circulation). The liquid stream which leaves the quench column is pumped to the upper part of a stripper column (C) in which a large fraction of the dissolved acrolein may be recovered. The residual liquid may then, for example, be fed into a thermal oxidation stage or a biological treatment unit for the disposal thereof.

The acrolein-rich gas from the upper part of column (B) is divided into two streams. The first stream is fed into an absorption column (D) in which the acrolein is absorbed in a liquid stream containing principally water. The amount of gas which flows through this column may be limited by the amount of recycling gas required for the reactor(s), in view of the fact that the low-acrolein gas which leaves the column is sent completely to the reactor(s) after a compression stage. The acrolein-rich water stream in the bottom of column D is fed into a distillation column (E) in which the acrolein is distilled, preferably under gentle vacuum conditions, in order to obtain a monophasic acrolein-rich mixture with water via the upper part of the column and a virtually acrolein-free water stream via the column bottom. This water stream may be partly sent back to the upper part of the absorption column (D) in order to require a minimum amount of additional water, with simultaneous reduction in the wastewater burdens. The stream passes through a heat exchanger, wherein the feed stream to the distillation column E may advantageously be heated, and a further series of heat exchangers, in order to achieve an end temperature between 0 and 20° C., preferably between 4 and 12° C. The acrolein-rich stream obtained in the upper part of the distillation column E preferably has a concentration close to the azeotropic composition.

The gaseous acrolein stream is condensed and utilized partly as reflux in the distillation column. The residual condensed acrolein (5) is sent without intermediate storage to the bottom of the reactor F, preferably a reactive absorption stage in the form of a reactive absorption column, in which a reaction is effected with methyl mercaptan to form MMP. In the absorption/distillation circuit, demineralized water is conducted in (10) in order to prevent the accumulation of reaction by-products in this circulation system. A purge stream (11) from this circulation system is discharged from the stream which is conducted out of the distillation column E in the direction of absorption column D. This purge stream can be conducted partly to the upper pumped circulation system of the quench column B in order to increase the ratio of liquid to gas in the middle section of the column and thus to achieve better by-product removal. The purge stream 11 can also be fed directly into a thermal oxidation stage or a biological treatment unit for disposal.

The other fraction of the acrolein-rich gas which leaves the column B is likewise fed into the reactor F. In this plant section, the acrolein is first absorbed in MMP and then reacts with methyl mercaptan (6) in the presence of a homogeneous catalyst (7) to form more MMP (excess methyl mercaptan ~1.005 mol/mol) than in the process according to DE 10 2010 064 250.9. Analogous to the system described in DE 10 2010 064 250.9, it may be possible to withdraw the MMP produced with a pump from the bottom of the column and then to cool it in two steps, first with cooling tower water (CTW) to ~35° C. and then with cooled water (CW) to <10° C. The cold MMP enters the upper part of the reactive absorption column and serves as an absorption medium.

Either after the first or second cooling stage, a fraction of the MMP leaves the process as product stream (8). A second pumped circulation stream using MMP is fed into the middle section of the column. The low temperatures which are employed in the upper part of the reactive absorption column contribute to a reduction in the acrolein, methyl mercaptan and MMP losses. The offgas which leaves the column may be disposed, for example, in a thermal oxidation stage. Upstream of the reactor, the gaseous and/or liquid acrolein stream arriving from the condenser of the distillation column E enters the system.

All heat exchangers shown in FIG. 1 may also represent a plurality of heat exchangers arranged in series or parallel, not necessarily using the same cooling media.

Figure 2:
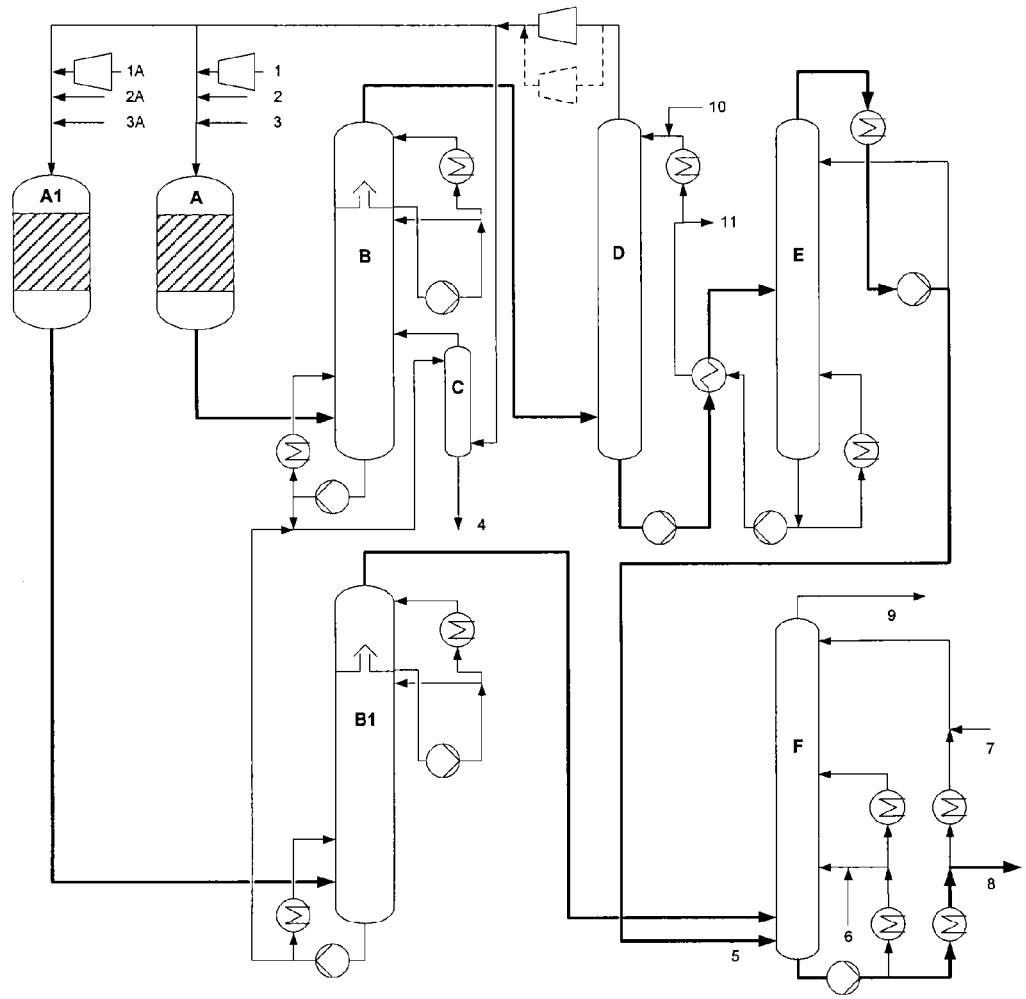
FIG. 2 shows the process flow diagram of the second embodiment according to the invention.

Description of Process According to FIG. 2

Alternatively, in another preferred embodiment of the invention, a process consisting of at least two separate acrolein reactors is conducted (FIG. 2). The gaseous hydrocarbon (3), preferably propylene, is fed together with compressed ambient air (1), small amounts of steam (2) and a low-oxygen recycling stream into the first shell-and-tube reactor (A), in which the partial oxidation reaction to give acrolein takes place. As described above under FIG. 1, in the first column (B), the acrolein-rich gases are cooled and freed of a large fraction of the by-products. The largest fraction of the acrolein dissolved in the wastewater stream leaving column B is recovered in the stripping column C. The gases which leave column B enter the absorber (D), in which the acrolein is absorbed in a liquid stream containing principally water. As in process option 1 of the invention, acrolein is distilled in column E and the liquid product stream is immediately fed into the reactor F (reactive absorption stage) without intermediate storage. Of the low-acrolein and low-oxygen gas which leaves column D, only the fraction required for the dilution of the mixture supplied from reactor A is recycled. The residual gas containing unconverted propylene is fed as diluent/inertization gas into a second acrolein reactor (A1), which is likewise provided with a separate air and propylene supply. The gas leaving reactor A1 enters column B1 through the base. B1 is of analogous construction to column B for the first reactor. The water stream leaving column B1 is sent to the stripping column C, in which a large fraction of the acrolein present in this stream may be recovered. The water stream leaving column C may be disposed of by thermal or biological means. The gases which leave column B1 through the top are fed directly into the reactive absorption stage F. In this plant section, the acrolein is first absorbed in MMP and then reacts with methyl mercaptan (6) in the presence of a homogeneous catalyst (7) to form more MMP (excess methyl mercaptan ~1.005 mol/mol), similarly to the embodiment which is described in DE102010064250.9. The MMP product stream is shown as stream 8. The offgases of the process (9) are sent to a thermal oxidation stage. Analogous to FIG. 1, demineralized water is added (10) to the absorption/distillation circuit in order to avoid the accumulation of reaction by-products in this circuit. A purge stream (11) from this circuit is discharged from the stream which leads out of the distillation column E in the direction of absorption column D. This purge stream may be conducted partly to the upper pumped circulation system of quench column B or B1, in order to increase the liquid to gas ratio in the middle column section and thus to achieve better by-product removal. The purge stream 11 may also be fed directly into a thermal oxidation stage or a biological treatment unit for disposal.

Comparison Between Different Process Configurations:

The results of a computer simulation based on the Aspen Plus simulation program (version 7.1) from Aspen Technology, Inc. are described hereinafter. The simulation is based on NRTL-HOC (Non-Random Two-Liquid model/Hayden O'Connell equation) and NRTL-RK (Non-Random Two-Liquid model/Redlich-Kwong equation) models. The necessary binary interaction parameters were partly estimated from in-house measurement data or from measurement data available in literature/material databases. In addition, the simulation has been validated with real plant data.

For the simulation calculation of the reaction stage, an acrolein yield based on the propylene feedstock of 81.02% was entered into the ASPEN program. The propylene conversion entered was 97.1%, based on a single pass in the process (analogously to configuration D or E).

The simulation results for several process configurations with regard to overall acrolein yield, propylene conversion, amount of offgas and liquid outflows, and the consumption values for steam and electricity, are compared. The process configurations are detailed as follows:

Configuration A (Comparative Example 1) corresponds to a conventional acrolein production process as described in Ullmann's Encyclopedia of Industrial Chemistry (Wiley-VCH Verlag, 2007, particularly pages 7-9), consisting of three main process blocks: a reaction step which includes a compressor stage for air, a compressor for recycling gas, a propylene vaporization unit and at least one shell-and-tube reactor with integrated post-cooler and steam generator; a process block for quenching and a by-product removal, consisting of at least one column, a wastewater stripper and the required heat exchange and pumping apparatus; and an absorption/distillation process step, consisting of an absorption column, a distillation column and the heat exchange and pumping apparatus needed. The greatest fraction of the absorption media is demineralized water. The acrolein was recovered as the top product of the distillation column with a composition close to the azeotropic composition (acrolein/water). The main impurity which was still present in the product is acetaldehyde. For the simulation runs, the amount of steam fed into the reactor was set to 0.19 kg/kg of propylene supplied. The outlet pressure selected for the fresh air and the recycling gas compressors was 2.7 bara. The compression was considered to be isentropic in the simulation (isentropic efficiency: 0.65/1.0 mechanical efficiency). The temperature of the fresh air at the entry point of the compressor was set to 30° C. In this configuration, the low-acrolein gas which leaves the absorption unit is partly reused as recycling gas in order to dilute the reaction mixture (dilution or inertization gas). The residual fraction of low-acrolein gas leaves the system and is designated as "offgas". There are two liquid outflows in the plant: one which leaves the stripping column of the quench and by-product removal step, and a much smaller one, which is a purge stream of the absorption/distillation step.

Configuration B (Example 1 according to the invention): This corresponds to the above-described process of the first embodiment. In analogy to configuration A, the compression pressure of the gas streams was set to 2.7 bara, and the amount of steam supplied to 0.19 kg/kg of propylene supplied. For this purpose, a propylene vaporization unit was also considered. All other process parameters relating to the pressure and the temperature in sections A/A1, B, C, D and E (FIG. 1) were identical to those selected in configuration A. The molar liquid flow rates, like those of the pumped circulation streams and of the absorption liquid phase, were set as a function of the total gas flow through the columns. In addition, the number of theoretical plates in the columns and the specific ratio of recycling gas/propylene supplied were the same as used in configuration A.

For the simulation calculations, the following flow rates were also used: the proportion of the stream from quench column B in the direction of the absorber/desorber system (column D) was 49.51% by weight, and the proportion to the reactive absorber (column F) 50.49% by weight.

In the plant section reactor F, the acrolein-containing gas stream coming from the quench column B is contacted with a mixture of MMP, MC, MMP/MC hemithioacetal and water. Analogously to the manner described in DE102010064250.9, the acrolein in this liquid mixture is absorbed and reacts in the presence of a catalyst with the free MC or with the MC which has been freed from the hemiothioacetal form of MC and MMP, in order to form more MMP. The reaction proceeds on the internals, and likewise in the liquid retained in the bottom of the column. The liquid acrolein stream from column E (5) is likewise added to the bottoms of column F.

Configuration C (Example 2 according to the invention): this corresponds to the process of the second embodiment (FIG. 2). The input parameters for the simulation relating to the pressure attained by the compressors, the steam supply ratio, the recycling gas ratio, the number of theoretical plates in the columns and the other parameters of pressure and temperature which apply to sections A/A1, B, C, D, E and F were kept at the same level in each case as in the configurations mentioned previously. The molar liquid flow rates, like those of the pumped circulation streams and of the absorption liquid phase, were adjusted as a function of the total gas flow rate. A propylene vaporization unit was also considered.

Configuration D (Comparative Example 2) corresponds to the process described in DE102010064250.9. In contrast to the above processes, this configuration does not make use of a recycling gas stream. The inert material is provided by an external source. The first process block (reaction) of this system consists of a compressor stage for air, a propylene vaporization unit, at least one shell-and-tube reactor with an integrated post-cooler and steam generator, and a compressor for the external inert gas stream. The reaction block is followed by a quench and by-product removal block similarly to the columns described, and peripheral components around columns B and C in the previous configurations. The last process block is analogous to column F and its peripheral components, which are already present in configurations B and C. It was stipulated in this case that the inert gas stream originates from an incineration unit which burns natural gas with ambient air as an oxidant. This offgas is at atmospheric pressure and is cooled before the compression from 160° C. to 50° C. in a heat transferer operated with cooling tower water. The gas contains 4.2 mol % of $O_2$ and 12.1 mol % of $H_2O$; the remainder is $N_2$ and $CO_2$. The feed gas composition at the inlet of the reactor, in terms of the propylene and oxygen concentrations, is comparable to those used in the previous configurations. The pressure and temperature conditions in the quench/by-product removal and absorption/reaction sections were the same as in configurations B and C. The molar liquid flow rates, like those of the pumped circulation streams, were matched to the conditions in configurations B and C as a function of the overall gas flow rate.

Configuration E (Comparative Example 3) corresponds to a system in which the external inert gas stream of configuration D is replaced by steam. Accordingly, the reaction process block in this configuration includes only one compressor for the air, a propylene vaporization unit and at least one shell-and-tube reactor with integrated post-cooler and steam generator. Downstream of the reaction block, the reaction gases enter a quench/by-product removal column which is analogous to columns B and C and the peripheral components thereof in the previous configurations. In the subsequent step, the purified gas stream is fed into the absorption/reaction system analogously to column F in the configurations so far. Since there is no other inert gas stream available in this configuration, nitrogen was used as the stripping medium in column C. The pressure and temperature conditions in the quench/by-product removal and absorption/reaction sections were the same as in configurations B and C. The liquid flow rates were adjusted as a function of the gas flow rates.

The results of the simulation examples are compiled in Table 1. Compared to the standard acrolein production process (configuration A), both inventive process designs which were presented here (configurations B and C) have an equivalent acrolein yield. The MMP yield is somewhat lower compared to the standard process due to the minimal amount of MMP which leaves the process with the offgas. However, due to the lack of recycling gas, both configurations with direct absorption/reaction of the acrolein produced in the MMP (configurations D and E) exhibit a much lower acrolein and MMP yield based on propylene. The product yields noticeably affect the overall production costs of MMP in view of the relatively high cost of propylene.

Inventive configurations B and C also have a nearly 50% lower steam consumption compared to the standard process, and about 30% lower than configuration E. Configuration D has no steam consumption whatsoever.

With regard to the cold water consumption to attain temperatures on the product side of <35° C. too, configurations B and C exhibit lower values than configuration A. Both configurations without distillative operation (D and E) exhibit even lower consumption values of cooled water.

It is also significant that configurations B and C produce similar amounts of liquid and gaseous outflows to the comparative process (configuration A). On the other hand, configuration D produces nearly twice the amount of offgas, while configuration E affords almost twice as high a wastewater flow rate, but with a much lower organic content. In the case of detoxification of this wastewater in an incineration plant, the disposal costs of this variant are much higher than all other processes depicted here.

Process configurations A to E presented were simulated with the aid of the program Aspen Plus (version 7.1) and a validated simulation. The packing with the same basic physicochemical character was used for the simulation of 3 alternative processes. The process simulated as configurations B and C according to the invention show a clear advantage over the conventional production process. Firstly, the intermediate storage of large volumes of acrolein is avoided; secondly, the process has a much lower consumption of steam and cooling media. Compared to processes based on the direct absorption/reaction of gaseous acrolein, which make use either of inert gases from an external source or of steam for the dilution of the reaction mixture entering the reaction step, the processes according to the invention have a much higher product yield and a smaller amount of waste streams (offgas in one case and wastewater in the other case).

Numerous modifications and variations on the present invention are possible in light of the above teachings. It is therefore to be understood that within the scope of the appended claims, the invention may be practiced otherwise than as specifically described herein.

TABLE 1

Results of the simulation runs for the different configurations evaluated

|  | Configuration A[2] | Configuration B/ process option 1 | Configuration C/ process option 2 | Configuration D | Configuration E |
|---|---|---|---|---|---|
| PE[1] converted/PE in [%] | 98.5 | 98.5 | 98.5 | 97.1 | 97.1 |
| mol Ac to product/100 mol PE | 82.0 | 82.0 | 82.0 | 80.7 | 80.6 |
| mol MMP/100 mol PE | 81.8 | 81.6 | 81.6 | 80.2 | 80.2 |
| Cooling tower water consumption[3] [kWh/100 kg MMP] | 59.4 | 49.4 | 48.8 | 55.0 | 80.8 |
| Cold water consumption[4] [kWh/100 kg MMP] | 62.5 | 50.6 | 50.9 | 38.6 | 31.9 |
| 6 bara steam consumption [kg/100 kg MMP] | 86.5 | 44.0 | 44.2 | 0.0 | 70.5 |
| Consumption of demin. water [kg/100 kg MMP] | 8.4 | 4.1 | 4.1 | 0.0 | 0.0 |
| Wastewater production [kg/100 kg MMP] | 48.8 | 43.8 | 43.7 | 44.2 | 101.3 |
| Offgas [kg/100 kg MMP] | 210.4 | 212.7 | 213.3 | 420.4 | 262.0 |
| Content of organic components in the wastewater [% by wt.] | 19.3 | 21.4 | 21.5 | 21.2 | 9.6 |
| Offgas desulphurization needed after incineration (Y/N) | N | Y | Y | Y | Y |
| Power consumption of compressors [kWh/100 kg MMP] | 17.3 | 17.2 | 17.2 | 20.7 | 12.3 |

[1] PE = propylene;
[2] A conventional process was assumed for the reaction of AC and MC to give MMP with a yield loss of 0.14% based on propylene;
[3] The minimum exit temperature of all heat exchangers operated with cooling tower water on the product side was set to 35° C. in the simulation.
[4] Cold water is a cooling medium for attaining necessary temperature levels which cannot be attained with cooling tower water (product side exit temperature <35° C.).

The invention claimed is:

1. A process to produce 3-methylmercaptopropionaldehyde, comprising:
   A) oxidizing a mixture of propylene and inert diluent gases with air over a heterogeneous catalyst to obtain a gaseous oxidation reaction mixture comprising acrolein and by-products;
   B) quenching the gaseous oxidation reaction mixture in a quench column to obtain a gas stream comprising acrolein and a quench liquid comprising residual acrolein and the by-products;
   C) recovering the acrolein by stripping from the quench liquid obtained in a lower portion of the quench column B) and returning the stripped acrolein to the quench B);
   D) absorbing a first portion of the gas stream comprising acrolein from the quench column B) in water to obtain an aqueous acrolein solution and an uncondensable gaseous stream comprising inert gases;
   D1) recycling at least a portion of the uncondensable gaseous stream to the oxidation A) to supply the inert diluent gases;
   E) distilling the acrolein from the aqueous acrolein solution to obtain an acrolein-free aqueous bottom product in column E;
   E1) condensing the distilled acrolein from E);
   F) reacting the distilled acrolein from E1) and a second portion of the gas stream comprising acrolein from quench column B) with methyl mercaptan in a mixture comprising at least one of 3-methylmercaptopropionaldehyde and a hemithioacetal of methyl mercaptan and 3-methylmercaptopropionaldehyde to obtain the 3-methylmercaptopropionaldehyde.

2. The process according to claim 1, wherein the oxidation A) is conducted in at least one shell-and-tube reactor and the reactor tube comprises the heterogeneous catalyst.

3. The process according to claim 2, further comprising cooling the shell-and-tube reactor with a salt bath, wherein a temperature of the salt bath is 300-400° C.

4. The process according to claim 1 wherein a temperature of the gaseous oxidation reaction mixture from A) is from 200 to 280° C. when quenched.

5. The process according to claim 1 further comprising:
   removing a substream of a condensate from an upper third of a quench column of B); and cooling the substream; and
   feeding the cooled substream back to the top of the column B.

6. The process according to claim 1, further comprising:
   removing a substream of the quench liquid from a bottom of a quench column B;
   cooling the substream; and
   feeding the cooled substream back to the lower third of the quench column B.

7. The process according to claim 1, wherein residual acrolein fractions recovered from C) are recycled into B).

8. The process according to claim 1, wherein a temperature of the absorption D) is from 1 to 25° C.

9. The process according to claim 1, wherein the distillation E) is operated at a pressure of 0.4 to 1.2 bara (bar absolute).

10. The process according to claim 1, further comprising; recycling the acrolein-free aqueous bottom product of the distillation to the absorption D).

11. The process according to claim 1, wherein the reaction F) of methyl mercaptan and acrolein is conducted with a catalyst comprising a base, and optionally further comprising an acid.

12. The process according to claim 11, wherein the catalyst comprises an optionally substituted N-heterocyclic amine or an amine of the formula NR1R2R3 wherein R1, R2 and R3 are each independently H, C1-C14-alkyl or C7-C14-aralkyl, with the proviso that, only one of R1, R2 and R3 may be H.

13. The process according to claim 11, wherein the basic catalyst comprises at least one amine base selected from the group consisting of pyridine, an alkyl-substituted pyridine, trimethylamine, triethylamine, tripropylamine, tributylamine, tridecylamine, tridodecylamine and dimethylbenzylamine.

14. The process according to claim 11, wherein the catalyst comprises an acid and the acid is selected from the group consisting of hydrochloric acid, sulphuric acid, phosphoric acid, formic acid, acetic acid, propionic acid, lactic acid, succinic acid, tartaric acid and citric acid.

15. The process according to claim 1, wherein a temperature of the reaction F is from 50 to 100° C. and a pressure of the reaction F is from 1.0 to 2.5 bara.

16. The process according to claim 1, wherein a proportion of the gas stream comprising acrolein B) in the reaction F) is 30-70% by weight of a total amount of the acrolein-containing gas from B).

17. The process according to claim 1, wherein the gas phase oxidation of propylene in A) is conducted in parallel in at least two oxidation reactors.

18. A process to produce 3-methylmercaptopropionaldehyde, comprising:
- A and A1) oxidizing a mixture of propylene and inert diluent gases with air over a heterogeneous catalyst in two streams to obtain a first A) and a second A1 gaseous oxidation reaction mixtures comprising acrolein and by-products;
- B) quenching the first gaseous oxidation reaction mixture from A) in a quench column to obtain a gas stream comprising acrolein and a quench liquid comprising residual acrolein and the by-products;
- B1) quenching the second gaseous oxidation reaction mixture from A1) in a quench column to obtain a gas stream comprising acrolein and a quench liquid comprising residual acrolein and the by-products;
- C) recovering the acrolein by stripping from the quench liquid obtained in a lower part of the quench column B) and returning the stripped acrolein to the quench;
- D) absorbing a first portion of the gas stream comprising acrolein from the quench column B) in water to obtain an aqueous acrolein solution and an uncondensable gaseous stream comprising inert gases;
- D1) recycling at least a portion of the uncondensable gaseous stream to the oxidation streams of A) and A1) to supply the inert diluent gases;
- E) distilling the acrolein from the aqueous acrolein solution from D) to obtain an acrolein-free aqueous bottom product;
- E1) condensing the distilled acrolein from E);
- F) reacting the distilled acrolein from E1) and the gas stream comprising acrolein from B1) with methyl mercaptan in a mixture comprising at least one of 3-methylmercaptopropionaldehyde and a hemithioacetal of methyl mercaptan and 3-methylmercaptopropionaldehyde to obtain the 3-methylmercaptopropionaldehyde.

19. The process according to claim 18, wherein the oxidation A) is conducted in at least one shell-and-tube reactor and the reactor tube comprises the heterogeneous catalyst.

20. The process according to claim 19, further comprising cooling the shell-and-tube reactor with a salt bath, wherein a temperature of the salt bath is 300-400° C.

21. The process according to claim 18 wherein a temperature of the gaseous oxidation reaction mixtures from A) and A1) is from 200 to 280° C. when quenched.

22. The process according to claim 18 further comprising:
removing a substream of a condensate from an upper third of a quench column of B) or B1); and cooling the substream; and
feeding the cooled substream back to the top of the column B) or B1).

23. The process according to claim 18, further comprising:
removing a substream of the quench liquid from a bottom of a quench column B) or B1);
cooling the substream; and
feeding the cooled substream back to the lower third of the quench column B) or B1).

24. The process according to claim 18, wherein residual acrolein fractions recovered from C) are recycled into B).

25. The process according to claim 18, wherein a temperature of the absorptions D) and D1) is from 1 to 25° C.

26. The process according to claim 18, wherein the distillation E) is operated at a pressure of 0.4 to 1.2 bara (bar absolute).

27. The process according to claim 18, further comprising; recycling the acrolein-free aqueous bottom product of the distillation to the absorption D).

28. The process according to claim 18, wherein the reaction F) of methyl mercaptan and acrolein is conducted with a catalyst comprising a base, and optionally further comprising an acid.

29. The process according to claim 28, wherein the catalyst comprises an optionally substituted N-heterocyclic amine or an amine of the formula NR1R2R3 wherein R1, R2 and R3 are each independently H, C1-C14-alkyl or C7-C14-aralkyl, with the proviso that, only one of R1, R2 and R3 may be H.

30. The process according to claim 28, wherein the basic catalyst comprises at least one amine base selected from the group consisting of pyridine, an alkyl-substituted pyridine, trimethylamine, triethylamine, tripropylamine, tributylamine, tridecylamine, tridodecylamine and dimethylbenzylamine.

31. The process according to claim 28, wherein the catalyst comprises an acid and the acid is selected from the group consisting of hydrochloric acid, sulphuric acid, phosphoric acid, formic acid, acetic acid, propionic acid, lactic acid, succinic acid, tartaric acid and citric acid.

32. The process according to claim 18, wherein a temperature of the reaction F) is from 50 to 100° C. and a pressure of the reaction F) is from 1.0 to 2.5 bara.

* * * * *